(12) United States Patent
Ohinata et al.

(10) Patent No.: US 11,464,824 B2
(45) Date of Patent: Oct. 11, 2022

(54) PEPTIDE CAPABLE OF IMPROVING COGNITIVE FUNCTION

(71) Applicant: THE FOOD SCIENCE INSTITUTE FOUNDATION, Tokyo (JP)

(72) Inventors: Kousaku Ohinata, Kyoto (JP); Akitoshi Nagai, Kyoto (JP); Daisuke Kozutsumi, Tokyo (JP)

(73) Assignee: THE FOOD SCIENCE INSTITUTE FOUNDATION, Tokyo (JP)

( * ) Notice: Subject to any disclaimer, the term of this patent is extended or adjusted under 35 U.S.C. 154(b) by 0 days.

(21) Appl. No.: 16/976,944

(22) PCT Filed: Mar. 1, 2019

(86) PCT No.: PCT/JP2019/008055
§ 371 (c)(1),
(2) Date: Aug. 31, 2020

(87) PCT Pub. No.: WO2019/168149
PCT Pub. Date: Sep. 6, 2019

(65) Prior Publication Data
US 2020/0390846 A1    Dec. 17, 2020

(30) Foreign Application Priority Data
Mar. 2, 2018    (JP) .............................. JP2018-037169

(51) Int. Cl.
| A61K 38/06 | (2006.01) |
| A61K 9/00 | (2006.01) |
| A61P 25/28 | (2006.01) |
| A23L 33/18 | (2016.01) |

(52) U.S. Cl.
CPC .............. *A61K 38/06* (2013.01); *A23L 33/18* (2016.08); *A61K 9/0056* (2013.01); *A61P 25/28* (2018.01); *A23V 2002/00* (2013.01)

(58) Field of Classification Search
CPC ... A23L 33/18; A23V 2002/00; A61K 38/018; A61K 38/06; A61K 9/0056; A61P 25/28
See application file for complete search history.

(56) References Cited

U.S. PATENT DOCUMENTS

| 2012/0277160 A1 | 11/2012 | Ohsawa et al. |
| 2017/0209520 A1 | 7/2017 | Ano et al. |
| 2020/0060993 A1 | 2/2020 | Soya et al. |

FOREIGN PATENT DOCUMENTS

| JP | 2012-12358 | 1/2012 |
| JP | 2012-31139 | 2/2012 |
| JP | 2012-508254 | 4/2012 |
| JP | 2014-189549 | 10/2014 |
| JP | 2015-154773 | 8/2015 |
| JP | 2017-8104 | 1/2017 |
| WO | 2010/056622 | 5/2010 |
| WO | 2013/034982 | 3/2013 |
| WO | 2017/213197 | 12/2017 |

OTHER PUBLICATIONS

Yau, Physical Exercise-Induced Adult Neurogenesis: A Good Strategy to Prevent Cognitive Decline in Neurodegenerative Diseases?, BioMed Research International vol. 2014, Article ID 403120, 20 pages.*
International Search Report dated May 21, 2019 in International (PCT) Application No. PCT/JP2019/008055 with English language translation.
Uchida et al., "Hippocampal nemogenesis effect and antidepressant effects of milk-derived peptide Tyr-Leu-Gly", Lecture abstracts of the 2014 conference of JSBBA, with partial English-language translation.
Nagai et al., "Milk-derived peptides improve cognitive decline associated with the intake of high-fat foods", Lecture abstracts of the 2018 conference of JSBBA, with partial English-language translation.
Mizushige et al., "Characterization of Tyr-Leu-Gly, a novel anxiolytic-like peptide released from bovine αs-casein", The FASEB Journal, Jul. 2013, vol. 27, No. 7, pp. 2911-2917.
Takashi Asada et al., "Prevalence of Dementia in Urban Areas and Measures for Daily-living Impairment in Dementia, Health and Labor Science Research Grants, Comprehensive Research Project on Measures for Dementia", Comprehensive Research Report 2011-2012, 2013, with partial English-language translation.
Yoshida et al., "Prevalence and Causes of Functional Disability in Elderly General Population of Japanese: The Hisayama Study", J Epidemiol., 2012, vol. 22, pp. 222-229.
Ozawa et al., "Milk and Dairy Consumption and Risk of Dementia in an Elderly Japanese Population: The Hisayama Study," J Am Geriatr Soc., 2014, vol. 62, pp. 1224-1230.
Ferreira et al., "Insulin Resistance in Alzheimer's Disease," Frontiers in Neuroscience, Nov. 2018, vol. 12, Article 830, pp. 1-11.

* cited by examiner

*Primary Examiner* — Julie Ha
*Assistant Examiner* — Erinne R Dabkowski
(74) *Attorney, Agent, or Firm* — Wenderoth, Lind 7 Ponack, L.L.P.

(57) ABSTRACT

An object of the present invention is to provide a peptide having an excellent effect in terms of preventing deterioration in cognitive function and improving cognitive function, and provide its usage. The present invention uses the tripeptide represented by Tyr-Leu-Gly as an active ingredient of a composition for improving cognitive function or a composition for promoting brain-derived neurotrophic factor expression in the hippocampus. These compositions include a food composition, a food additive composition, and a pharmaceutical composition.

8 Claims, 3 Drawing Sheets

PEPTIDE CAPABLE OF IMPROVING COGNITIVE FUNCTION

TECHNICAL FIELD

The present invention relates to a peptide that prevents deterioration in cognitive function and improves cognitive function. The present invention also relates to a composition comprising the peptide and its production method.

BACKGROUND ART

In 2012, the Ministry of Health, Labor and Welfare reported estimates that, in Japan, 4.62 million patients suffer from dementia, and 4 million patients suffer from mild cognitive impairment (MCI). The numbers are estimated to increase year by year (Non-patent Literature (NPL) 1). Dementia is a major cause of disability in activities of daily living (ADL), which are basic activities essential for daily life (e.g., eating, changing clothes, moving, excreting, grooming, and bathing) (NPL 2), and significantly deteriorates the quality of life of the elderly and caregivers such as families caring for the elderly. Therefore, preventing the development of dementia is a socially important issue.

Although large-scale epidemiological studies show that intake of milk or dairy products is a protective factor for dementia (NPL 3), its mechanism remains unclear. On the other hand, it has been reported that specific peptides from milk proteins can enhance memory and learning functions, and/or cognitive functions (Patent Literature (PTL) 1 to 4). However, although the tripeptide represented by Tyr-Leu-Gly obtained by digesting αs-casein, which is a milk protein, with an enzyme has been reported to have an anxiolytic effect (NPL 4), its effects on episodic memory, spatial memory, and brain-derived neurotrophic factor (BDNF) have not yet been clarified.

CITATION LIST

Patent Literature

PTL 1: JP2017-008104A
PTL 2: JP2012-012358A
PTL 3: JP2015-154773A
PTL 4: JP2012-031139A

Non-Patent Literature

NPL 1: Takashi ASADA et al., 2013, Prevalence of Dementia in Urban Areas and Measures for Daily-living Impairment in Dementia, Health and Labor Science Research Grants, Comprehensive Research Project on Measures for Dementia, Comprehensive Research Report 2011-2012
NPL 2: Yoshida D et al. 2012, J Epidemiol. 22: 222-229.
NPL 3: Ozawa M et al., 2014, J Am Geriatr Soc., 62:1224-1230.
NPL 4: Mizushige T, Sawashi Y, Yamada A, Kanamoto R, Ohinata K, Characterization of Tyr-Leu-Gly, a novel anxiolytic-like peptide released from bovine αS-casein, FASEB J., 2013 July; 27(7): 2911-7. doi: 10.1096/fj.12-225474. Epub 2013 Apr. 11.
NPL 5: Lais S. S. Ferreira et al., Insulin Resistance in Alzheimer's Disease, Frontiers In Neuroscience, November 2018, Vol. 12, Article 830, 1-11

SUMMARY OF INVENTION

Technical Problem

An object of the present invention is to provide a peptide that has an excellent effect in terms of preventing deterioration in brain functions, in particular, cognitive function and improving cognitive function, and provide its usage. More specifically, an object of the present invention is to provide a composition, in particular, a food composition and a pharmaceutical composition comprising the peptide as an active ingredient, the compositions being for improving cognitive function, and provide production methods for the compositions.

Solution to Problem

To solve the above problems, the present inventors conducted extensive research using mice with deterioration in cognitive function induced by a high-fat diet, and confirmed that oral administration of the tripeptide represented by Tyr-Leu-Gly (also referred to below as "the YLG peptide" or simply as "the YLG") to the mice prevents an episodic and spatial memory decrease induced by a high-fat diet and improves both episodic and spatial memory. The inventors also confirmed that oral administration of the YLG peptide to the same mice prevents a hippocampal neurogenesis decrease induced by a high-fat diet and improves hippocampal neurogenesis. Since oral administration of the YLG peptide to the same mice promotes and improves the gene expression in the hippocampus of brain-derived neurotrophic factor (also simply referred to below as "BDNF"), which contributes to the promotion of neurogenesis, one of the reasons that a hippocampal neurogenesis decrease is prevented by the YLG peptide is believed to be also that BDNF gene (mRNA) expression is promoted in the hippocampus. Based on these findings, the present inventors concluded that YLG peptide intake can improve cognitive functions, which are deteriorated by diseases such as dementia or with age, and completed the present invention. The present invention has been completed based on these findings and encompasses the following embodiments.

(I) Composition for Improving Cognitive Function and Composition for Promoting BDNF Expression (I-1) A composition for improving cognitive function, the composition comprising an YLG peptide.
(I-2) A composition for promoting BDNF expression in the hippocampus, the composition comprising an YLG peptide.
(I-3) The composition according to (I-1) or (I-2), which is a food composition, a food additive composition, or a pharmaceutical composition.
(I-4) The composition according to (I-1) or (I-2), which is a health food, a functional food, a dietary supplement, a supplement, a health-promoting food, a food for specified health use, a food with nutrient function claims, a food with functional claims, or a food for the sick.

(II) Method for Producing Composition for Improving Cognitive Function (II-1) A method for producing a composition for preventing deterioration of cognitive function and improving cognitive function, the method comprising adding an YLG peptide to a composition for preventing deterioration in cognitive function and improving cognitive function. The composition includes a composition for promoting BDNF expression. That is, the composition includes a composition for preventing deterioration in cognitive function and improving cognitive function through promotion of BDNF expression.

(II-2) The production method according to (II-1), wherein the YLG peptide is a peptide obtained by hydrolysis of a protein contained in a food or a food material.

(II-3) The production method according to (II-2), wherein the protein is a milk protein.

(II-4) The production method according to (II-2), wherein the YLG peptide is obtained by enzymatically treating a milk protein, or a food or a food material that contains a milk protein, with a microorganism-derived enzyme agent.

(II-5) The production method according to any one of (II-1) to (II-4), wherein the composition for improving cognitive function is a food composition, a food additive composition, or a pharmaceutical composition.

(II-6) The production method according to (II-5), wherein the food composition is a health food, a functional food, a dietary supplement, a supplement, a health-promoting food, a food for specified health use, a food with nutrient function claims, a food with functional claims, or a food for the sick.

(III) Use of YLG Peptide (III-1) Use of an YLG peptide in the manufacture of a composition for improving cognitive function.

(III-2) Use of an YLG peptide in the manufacture of a composition for promoting BDNF expression in the hippocampus.

(III-3) The use of an YLG peptide according to (III-1) or (III-2), wherein the composition is a food composition, a food additive composition, or a pharmaceutical composition.

(III-4) The use of an YLG peptide according to (III-3), wherein the food composition is a health food, a functional food, a dietary supplement, a supplement, a health-promoting food, a food for specified health use, a food with nutrient function claims, a food with functional claims, or a food for the sick.

(IV) YLG Peptide or YLG Peptide-Containing Composition (IV-1) An YLG peptide or YLG peptide-containing composition for use in preventing deterioration in cognitive function and improving cognitive function. The YLG peptide or YLG peptide-containing composition includes an YLG peptide or YLG peptide-containing composition for use in preventing or improving diseases or symptoms caused by deterioration in cognitive function, for example, memory impairment, such as dementia (cerebrovascular dementia, Alzheimer's disease) and amnesia (diminished memory).

(IV-2) An YLG peptide or YLG peptide-containing composition for use in promoting BDNF expression in hippocampus.

(IV-3) The YLG peptide or YLG peptide-containing composition according to (IV-1) or (IV-2), wherein the composition is a food composition, a food additive composition, or a pharmaceutical composition.

(IV-4) The YLG peptide or YLG peptide-containing composition according to (IV-3), wherein the food composition is a health food, a functional food, a dietary supplement, a supplement, a health-promoting food, a food for specified health use, a food with nutrient function claims, a food with functional claims, or a food for the sick.

(V) Method for Improving Cognitive Function (V-1) A method for preventing deterioration in cognitive function and improving cognitive function in a subject suffering from deterioration in cognitive function or a subject with signs of deterioration in cognitive function, the method comprising administering an YLG peptide or an YLG peptide-containing composition to the subject.

(V-2) The method according to (V-1), which is for preventing deterioration in cognitive function and improving cognitive function through promotion of BDNF expression.

(V-3) The method according to (V-1) or (V-2), wherein the composition is a food composition, a food additive composition, or a pharmaceutical composition.

(V-4) The method according to (V-3), wherein the food composition is a health food, a functional food, a dietary supplement, a supplement, a health-promoting food, a food for specified health use, a food with nutrient function claims, a food with functional claims, or a food for the sick.

Advantageous Effects of Invention

The present invention can provide a peptide having an excellent effect in terms of improving cognitive function and provide its usage. Specifically, the present invention can provide a composition, in particular, a food composition, a food additive composition, and a pharmaceutical composition that are suitably used for preventing deterioration in cognitive function and maintaining or ameliorating cognitive function. The composition for improving cognitive function of the present invention effectively prevents deterioration in cognitive function and improves cognitive function, in particular, cognitive function relating to episodic memory and/or cognitive function relating to spatial memory.

Further, the present invention can provide a composition, in particular, a food composition, a food additive composition, and a pharmaceutical composition that are suitably used for preventing a decrease in hippocampal neurogenesis and maintaining or promoting hippocampal neurogenesis. The present invention can further provide a composition, in particular, a food composition, a food additive composition, and a pharmaceutical composition that are suitably used for preventing a decrease in expression of brain-derived neurotrophic factor (BDNF) mRNA in the hippocampus and maintaining or promoting BDNF expression. An increase in BDNF expression in the hippocampus prevents a decrease in hippocampal neurogenesis and prevents deterioration in cognitive function, suitably achieving maintenance or amelioration of cognitive function.

DESCRIPTION OF EMBODIMENTS (I) Composition of the Present Invention

The composition for improving cognitive function of the present invention and the composition for promoting BDNF expression of the present invention are characterized by comprising an YLG peptide as an active ingredient.

The term "cognitive function" as used in the present invention refers to cognitive function relating to, at the very least, episodic memory evaluated according to an episodic memory evaluation test (object recognition test (ORT)) and/or spatial memory evaluated according to a spatial memory evaluation test (object location test (OLT)), both tests known as a behavioral test that examine the cognitive function in mammals. The expression "improving cognitive function" means preventing deterioration in cognitive function and improving cognitive function, in particular, brain functions associated with memory, i.e., episodic memory and/or spatial memory. In the present invention, the term "prevent" encompasses the meanings of suppressing and inhibiting. The term "improve" encompasses the meanings of maintaining and ameliorating. Therefore, in the present invention, the phrase "improving cognitive function" encompasses at least one of the following: preventing deterioration in cognitive function, maintaining cognitive function by preventing deterioration in cognitive function, and ameliorating cognitive function to prevent deterioration in cognitive function (or to maintain cognitive function). The phrase "improving cognitive function" also includes, for example, recovery of cognitive ability that has deteriorated, and recovery from symptoms that have shown signs of deterioration.

The "cognitive function" targeted by the present invention includes memory and learning functions without departing from the above description. In this case, "improving cognitive function" includes preventing a decrease in memory and learning ability that occurs with age in the elderly and the like, and improving memory and learning ability.

As shown in Experimental Example 1 below, the mechanism of action of the YLG peptide is assumed to be as follows. Specifically, a decrease in BDNF mRNA expression in the hippocampus is prevented, or BDNF mRNA expression is promoted or ameliorated, which consequently leads to enhancement of cognitive function, such as prevention of deterioration in cognitive function or amelioration of cognitive function. As a result of preventing a decrease in BDNF mRNA expression, or promoting or ameliorating BDNF mRNA expression, enhancement of cognitive function is also expected, including amelioration of memory and learning functions, such as prevention of a decrease in memory caused by aging. In that sense, the composition for improving cognitive function of the present invention can be referred to as a "composition for promoting BDNF expression in the hippocampus" (composition for promoting BDNF expression).

In the present invention, the expression "promoting BDNF expression" means that a decrease in BDNF mRNA expression in the hippocampus of mammals is prevented, and encompasses at least one of the following: preventing a decrease in BDNF expression, maintaining the BDNF level in the hippocampus by preventing a decrease in BDNF expression, and promoting or ameliorating BDNF expression to prevent a decrease in the BDNF level (or to maintain the BDNF level).

As shown in Experimental Example 1 below, prevention of a decrease in hippocampal neurogenesis is assumed to consequently lead to prevention of deterioration in cognitive function and improvement in cognitive function. Further, prevention of a decrease in hippocampal neurogenesis is also expected to consequently lead to enhancement of cognitive function, including amelioration of memory and learning functions, such as prevention of a decrease in memory caused by aging.

Furthermore, as shown in Experimental Example 2 below, the YLG peptide has an effect in terms of improving insulin resistance induced by high-fat diet intake (diabetes improvement effect). Alzheimer's disease, a type of dementia, is also called "insulin resistance in the brain"; insulin sensitivity and Alzheimer's disease are known to be closely associated with each other (NPL 5). Therefore, the YLG peptide is believed to also prevent deterioration in cognitive function and improve cognitive function as a result of improvement in insulin resistance.

The YLG peptide used in the present invention may be a chemically synthesized peptide. The YLG peptide may also be a peptide obtained by chemically or enzymatically hydrolyzing proteins, polypeptide raw materials, etc. from milk, soybeans, wheat, eggs, meat, fish meat, seafood, and the like. Specifically, since the YLG peptide sequence is contained in at least milk proteins, in particular, αs-casein in whey of milk, the YLG peptide can be produced by subjecting a food or food material containing αs-casein to acid hydrolysis, enzymatic treatment with protease, microbial fermentation, or the like. As the composition of the present invention, the resulting preparation (YLG peptide-containing protein hydrolysate) may be used as is, or may be used after concentration, or as a dry powder after spray drying, freeze drying, or the like. It is also possible to perform purification to any degree before use, such as removing impurities, salts, enzymes, etc., if necessary.

The amino acids constituting the YLG peptide may be composed only of L-type amino acids or composed only of D-type amino acids as long as the effects of the present invention can be achieved. Alternatively, the peptide may be composed of a mixture of L-type amino acids and D-type amino acids. Further, the peptide may be composed only of naturally occurring amino acids, may be composed only of modified amino acids to which optional functional groups are added, such as phosphorylated or glycosylated amino acids, or may be a peptide in which both of these amino acids are mixed. When the peptide contains two or more asynetric carbon atoms, enantiomers, diastereomers, or mixtures of enantiomers and diastereomers are usable.

Furthermore, the YLG peptide may be in the form of a pharmaceutically acceptable salt thereof or a solvate thereof as long as the effects of the present invention are exhibited. In that case, in the present invention, the term "YLG peptide" includes pharmaceutically acceptable salts of the YLG peptide and solvates of the YLG peptide. The pharmaceutically acceptable salts as used herein include acid addition salts, metal salts, ammonium salts, and organic amine addition salts. Specific examples of pharmaceutically acceptable acid addition salts include inorganic acid salts, such as hydrochloride, sulphate, and phosphate; organic acid salts, such as acetate, maleate, fumarate, citrate, and methanesulfonate; and the like. Examples of pharmaceutically acceptable metal salts include alkali metal salts, such as sodium salt and potassium salt; alkaline earth metal salts, such as magnesium salt and calcium salt; zinc salt; and the like. Examples of pharmaceutically acceptable ammonium salts include salts of ammonium, tetramethylammonium, and the like. Examples of pharmaceutically acceptable organic amine addition salts include addition salts of morpholine, piperidine, and the like.

The usage form of the YLG peptide is not particularly limited as long as it is used according to the usage of the present invention. For example, the YLG peptide can be used as a medicinal drug, an additive for adding to medicinal drugs, a food, an additive for adding to foods, and the like. The term "food" as used herein is synonymous with food and beverage, and is used in a broad sense including beverages. The term "food" in the present invention includes not only foods for humans but also foods for animals, such as pets and livestock (thus including feed and experimental feed).

(A) Application to Foods, Food Additives, and Medicinal Drugs

As described above, the YLG peptide of the present invention or a food ingredient containing the YLG peptide (e.g., a hydrolysate of milk protein) has an effect of improving cognitive function, in particular, episodic memory and/or spatial memory, and can be used for preventing or improving diseases or symptoms caused by deterioration in cognitive function, including, for example, dementia (cerebrovascular dementia, Alzheimer's disease, etc.). The YLG peptide of the present invention can also be used when amnesia is observed while the above diseases have not yet developed. Amnesia refers to diminished memory and is a memory disorder. Further, the YLG peptide of the present invention or a food ingredient containing the YLG peptide (e.g., a hydrolysate of milk protein) has an effect of preventing a decrease in BDNF expression or hippocampal neurogenesis by promoting BDNF expression in the hippocampus. The YLG peptide of the present invention or a food ingredient containing the YLG peptide can thus be used to prevent deterioration in memory and learning ability and improve memory and learning ability.

In order for the YLG peptide to effectively act on humans or animals, the composition of the present invention preferably comprises the YLG peptide in an amount of 0.00001 to 100 mass %, more preferably 0.0001 to 100 mass %, and most preferably 0.001 to 100 mass %. In addition to the YLG peptide, the composition of the present invention may further comprise one or more other active ingredients for improving cognitive function. The composition of the present invention may be administered or ingested in combination with the one or more other active ingredients, in addition to the YLG peptide. For example, the active ingredients may be compounds or compositions known to have an effect of, for example, maintaining or ameliorating cognitive function. Specific examples include docosahexaenoic acid (DHA), *Ginkgo biloba* extract, and the like. Examples of components that reduce amyloid β include anti-amyloid β antibodies and the like.

(A-1) Application to Foods and Food Additive Compositions

Examples of the usage form of the composition of the present invention include a food composition and a food additive composition. The forms of the food composition and the food additive composition are not particularly limited, and may be a liquid, a semi-liquid (including paste, gel, and sol), or a solid. A beverage-like form is also possible. The food composition includes health foods, functional foods, dietary supplements, supplements, as well as health-promoting foods, such as foods with disease risk reduction claims (foods for specified health use, nutritionally functional foods, foods with functional claims) and foods for the sick. For example, it is possible to subject a food material, such as milk, to microbial fermentation to obtain a dairy product, such as yogurt or cheese, or a koji-fermented product, containing the peptide. The supplement may be in the form of tablets produced by kneading a dry powder of the YLG peptide with an excipient, a binder, and the like and then tableting the mixture. The supplement may also be in the form of powders, pills, capsules, jellies, granules, and the like. In addition to the YLG peptide or a YLG peptide-containing protein hydrolysate, the food composition of the present invention can appropriately comprise components for foods (edible components), such as carbohydrates, proteins, lipids, vitamins, minerals, sugars (e.g., glucose), natural or artificial sweeteners, citric acid, carbonated water, fruit juice, stabilizers, preservatives, binders, thickeners, and/or emulsifiers.

When the food composition of the present invention is a beverage, examples of non-alcoholic beverages include, but are not limited to, mineral water, near water, sports drinks, tea beverages, milk beverages, coffee beverages, fruit juice-containing beverages, vegetable juice-containing beverages, fruit juice and vegetable juice beverages, carbonated beverages, and the like. Examples also include a beer beverage having an alcohol content of less than 1%, such as non-alcoholic beer. Mineral water may be carbonated or non-carbonated.

The tea beverages among the non-alcoholic beverages refer to beverages for drinking by brewing the leaves of a tea plant, which is an evergreen tree belonging to the genus *Camellia*, (tea leaves) or leaves of plants other than a tea plant, or by brewing grains. The tea beverages include fermented tea, semi-fermented tea, and non-fermented tea. Specific examples of the tea beverages include Japanese tea (e.g., green tea and barley tea), black tea, herbal tea (e.g., jasmine tea), Chinese tea (e.g., Chinese green tea and oolong tea), hojicha (Roasted green tea), and the like. The milk beverages include raw milk, milk, and the like, as well as beverages produced using, as a principal raw material, a food produced by using raw milk, milk, etc. In addition to those obtained by using milk or the like itself, milk beverages include, for example, those made from processed milk, such as nutrient-fortified milk, flavor-added milk, and sugar-decomposed milk.

When the present invention is used as a food composition, its daily intake amount converted to an intake amount of the YLG peptide is preferably 0.1 mg to 5 g per adult human. The daily intake amount is preferably 1 mg to 1 g, and more preferably 10 mg to 0.5 g. When the food composition of the present invention is added to containers each containing a single meal, the containers can each contain the food composition such that the YLG peptide is contained in an amount converted to an YLG peptide intake amount per single meal of, for example, 0.1 mg to 5 g, preferably 1 mg to 1 g, and more preferably 10 mg to 0.5 g.

The food composition of the present invention may further comprise a combination of the following other materials and compounds that are known to have an effect of improving brain functions. Examples include food ingredients, such as Ginkgo biloba extract, arachidonic acid (ARA), GABA, theanine, ceramide, caffeine, carnitine, α-glycerylphosphorylcholine (α-GPC), Bacopa monniera, DHA-binding phospholipids, phosphatidylserine (PS), phosphatidylcholine, St. John's wort, astaxanthin, niacin, pyrroloquinoline quinone (PQQ), and coenzyme Q10 (CoQ10); unsaturated fatty acids, such as docosahexaenoic acid (DHA) and eicosapentaenoic acid (EPA); polyphenols, such as resveratrol; chlorogenic acid; catechins; and the like. The amounts of these materials and compounds to be incorporated are within the known ranges for which their efficacy has been confirmed.

The food composition of the present invention, that is, the food composition for preventing deterioration in cognitive function and improving cognitive function, and the food composition for preventing a decrease in BDNF expression in the hippocampus and improving or promoting BDNF expression in the hippocampus, can be produced by adding the YLG peptide or YLG peptide-containing composition (food additive composition) to a composition for the above purposes (for improving cognitive function or promoting BDNF expression). The production method can be performed according to a standard production method for each food composition, except that the method comprises the step of adding the YLG peptide or YLG peptide-containing composition. As described above, the YLG peptide includes YLG peptides obtained by hydrolyzing proteins contained in a food or food material, preferably milk proteins, and more preferably casein.

The target to whom the food composition of the present invention is applied include those in need of preventing deterioration in cognitive function and improving cognitive function. Specifically, the food composition of the present invention is applicable to those who have symptoms caused by deterioration in cognitive function (e.g., diminished memory, diminished learning ability), those who have signs of these symptoms, and those who are potential to develop a disease caused by deterioration in cognitive function (e.g., cerebrovascular dementia, dementia, such as Alzheimer's disease, and a memory disorder, such as amnesia).

(A-2) Application to Medicines

Examples of the usage form of the composition of the present invention include a pharmaceutical composition. The composition in the form of a pharmaceutical composition can be produced, for example, by adding the YLG peptide as an active ingredient and mixing with a pharmaceutically acceptable carrier or additives, such as a carrier, an excipient, a binder, and a diluent, according to a standard method. The pharmaceutical composition can be administered orally or parenterally. Examples of the form for oral administration include granules, powders, tablets, pills, capsules, syrups, and the like. Examples of the form for parenteral administration include injections, drops, nasal preparations, enteral administration (tube administration), external preparations, and the like. The forms are not limited to these. The pharmaceutical composition is preferably used for oral administration.

Pharmaceutically acceptable carriers include excipients and diluents. Examples include dextrans, saccharose, lactose, maltose, xylose, trehalose, mannitol, sorbitol, gelatin, carboxymethyl cellulose, carboxyethyl cellulose, hydroxypropylmethyl cellulose, gum arabic, guar gum, tragacanth, acrylic acid copolymers, ethanol, saline, Ringer's solution, and the like.

In addition to the carriers, it is possible to add additives, such as preservatives, stabilizers, binders, pH adjusters, buffers, thickeners, gelling agents, and antioxidants.

These additives are preferably those that are used in the pharmaceutical production.

The pharmaceutical composition of the present invention may be used in combination with another medicinal drug that has an effect of improving brain functions. Examples of such medicinal drugs include the following, and commercially available medicinal drugs are preferable: dementia therapeutic agents, such as acetylcholinesterase inhibitors (donepezil, galantamine, rivastigmine, tacrine, etc.), NMDA receptor antagonists (e.g., memantine), and the like; and anxiolytics, such as benzodiazepine anxiolytic. These medicinal drugs may be administered simultaneously with, before, or after the administration of the pharmaceutical composition of the present invention. For a commercially available medicinal drug, the dose is preferably as instructed by the pharmaceutical manufacturer.

The dose of the pharmaceutical composition of the present invention varies depending on the administration form, the age and weight of the patient, the nature or severity of symptoms to be treated, etc. The dose for usual oral administration converted to a dose of the YLG peptide is preferably, for example, 0.01 mg to 1 g per day per adult human. The dose is preferably 0.1 mg to 0.5 g, and more preferably 1 mg to 100 mg. The dose may be appropriately selected according to various conditions, such as the route of administration. The administration can be performed in a single dose per day or in multiple divided doses per day for each subject. The subject as used in the present specification is usually a human. However, the subject also includes manuals other than humans, for example, pet animals, such as dogs.

The applicable diseases are the symptoms and diseases mentioned above caused by deterioration in cognitive function, such as dementia (e.g., cerebrovascular dementia and Alzheimer's disease). That is, the patient to whom the pharmaceutical composition of the present invention is applied is a person suffering from the diseases or symptoms described above. The pharmaceutical composition of the present invention is also applicable to patients with signs of the symptoms, patients suspected of suffering from the diseases, and patients with potential to develop the diseases.

The pharmaceutical compositions according to the present invention, i.e., the pharmaceutical composition for preventing deterioration in cognitive function and improving cognitive function, and the pharmaceutical composition for preventing a decrease in BDNF expression in the hippocampus and improving or promoting BDNF expression in the hippocampus, can be produced by adding the YLG peptide or YLG peptide-containing composition to a pharmaceutical composition for the purposes described above (improving cognitive function or promoting BDNF expression). This production method can be performed according to a standard production method for each pharmaceutical composition, except that the method comprises the step of adding the YLG peptide or YLG peptide-containing composition. As mentioned above, the YLG peptide includes YLG peptides obtained by hydrolyzing proteins contained in a food or food material, preferably milk proteins, and more preferably casein.

EXAMPLES

The present invention is described below with reference to Experimental Examples. However, the present invention is not limited to these Experimental Examples.

Experimental Example 1

Four-week-old male dd Y mice were divided into 3 groups (8 mice per group). The mice were reared for 1 week such that Group 1 was fed a normal diet (3.85 kcal/g: 20 kcal % of protein, 70 kcal % of carbohydrate, and 10 kcal % of lipid), and Group 2 and Group 3 were fed a 60% high-fat diet (5.24 kcal/g: 20 kcal % of protein, 20 kcal % of carbohydrate, and 60 kcal % of lipid). During the period, the YLG tripeptide was orally administered to Group 3 daily in an amount of 10 mg/kg/day.

Group 1: normal diet group (CD group)

Group 2: high-fat diet group (HFD group)

Group 3: high-fat diet+YLG administration group (HFD+YLG group)

On day 6 and day 7 after the initiation of feeding, two behavioral tests (episodic memory evaluation test: object recognition test (ORT), and a spatial memory evaluation test: object location test (OLT)), which are known as cognitive function evaluation systems, were performed, as well as a hippocampal neurogenesis evaluation test using deoxyuridine bromide (BrdU). On day 7, the brain hippocampus was removed, and a BDNF mRNA expression level in the hippocampus was measured.

(1) Episodic Memory Evaluation Test: Object Recognition Test (ORT): See FIG. 1.

(1-1) Test Method

Figure 1:
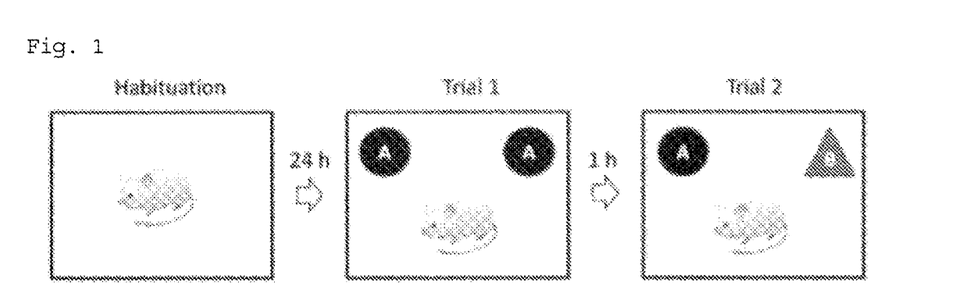
FIG. 1 is diagrams illustrating the details of a behavioral test (object recognition test (ORT)) conducted in Experimental Example 1 (1) (habituation trial (Habituation), acquisition trial (Trial 1), and test trial (Trial 2)).

The ORT is a behavioral test that evaluates episodic memory, which is part of cognitive functions. As shown in FIG. 1, the test includes three trials, i.e., a habituation trial (Habituation), an acquisition trial (Trial 1), and a test trial (Trial 2). First, the mouse was placed in a square open field for 5 minutes for habituation. After 24 hours, an acquisition trial (Trial 1) was performed. In Trial 1, two identical objects were placed in the square open field, and the mouse was allowed to freely explore the objects. When the total exploration time for the two objects reached 20 seconds, the mouse was removed from the square open field. One hour later, the test trial (Trial 2) was performed. In Trial 2, one of the two objects placed in the square open field was replaced with a novel object with a different shape, and the mouse was placed again in the square open field. In Trial 2, the approach time of the mouse for each object was measured. The ORT is an experimental system that evaluates cognitive function based on the fact that a mouse will spend a longer period of approach time at the novel object replaced in Trial 2 if the mouse remembers the shape of the objects in Trial 1. The cognitive function of the mice was evaluated using the ratio of the approach time for the novel object to the total approach time for both objects as an index. The habituation trial was performed on day 6 after the initiation of feeding, and Trial 1 and Trial 2 were performed on day 7.

(1-2) Test Results

Figure 2:
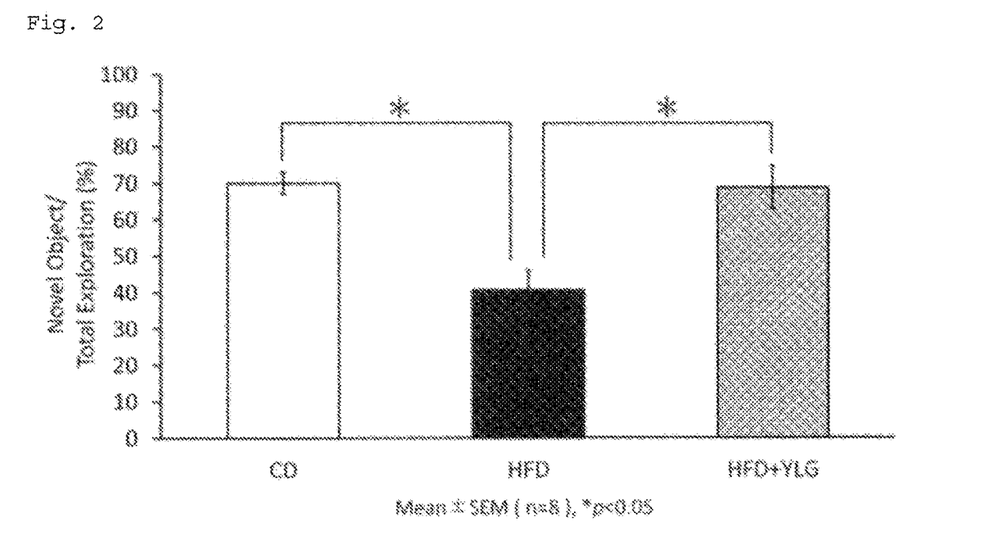
FIG. 2 shows the results of the ORT. In the figure, "D" represents a normal diet group, "HFD" represents a high-fat diet group, and "HFD+YLG" represents a group administered a high-fat diet and YLG (the same applies to FIGS. 4 to 6). The results are expressed as a ratio (%) of the approach time for a novel object to the total approach time for two objects placed in a square open field (vertical axis).

FIG. 2 shows the test results. As shown in FIG. 2, the results of the object recognition test (ORT), which evaluates episodic memory, clarified that the high-fat diet group (HFD group) showed a decrease in the approach time for the novel object (cognitive function deteriorated), compared to the normal diet group (CD group). However, the group administered a high-fat diet and the YLG (HFD+YLG group), in which the YLG peptide was orally administered daily while the high-fat diet was fed, showed an increase in the approach time, and its level recovered to a level equal to that of the normal diet group (CD group) (cognitive function improved). This suggests that oral administration of the YLG peptide improves episodic memory decreased by a high-fat diet.

(2) Spatial Memory Evaluation Test: Object Location Test (OLT): See FIG. 3.

(2-1) Test Method

Figure 3:
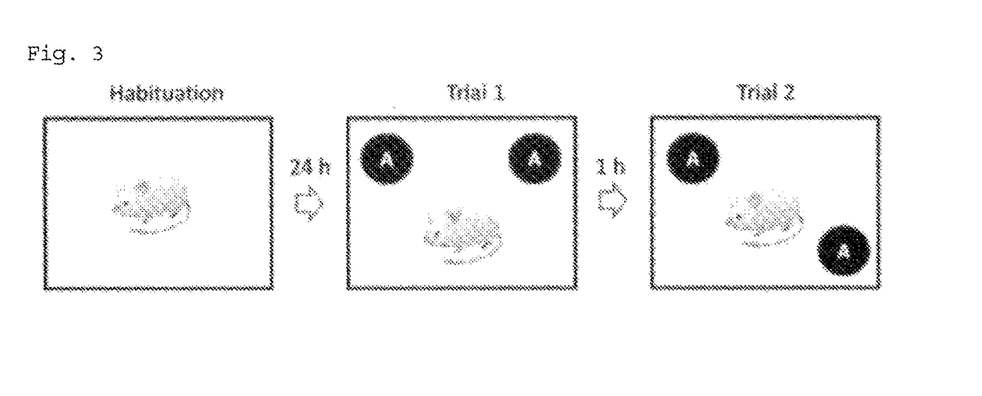
FIG. 3 is diagrams illustrating the details of a behavioral test (object location test (OLT)) conducted in Experimental Example 1 (2) (habituation trial (Habituation), acquisition trial (Trial 1), and test trial (Trial 2)).

The OLT is a behavioral test that evaluates spatial memory, which is part of cognitive functions. As shown in FIG. 3, this test includes three trials, i.e., a habituation trial (Habituation), an acquisition trial (Trial 1), and a test trial (Trial 2), as in the ORT test method described above in (1-1). The difference lies in that the location of only one object is changed in Trial 2. The OLT is an experimental system that evaluates cognitive function based on the fact that a mouse will spend a longer period of approach time for the object whose location is changed in Trial 2 if the mouse remembers the location of the objects in Trial 1. The cognitive function of the mice was evaluated using the ratio of the approach time for the object placed at the novel location to the total approach time for both objects as an index. The habituation trial was performed on day 6 after the initiation of feeding, and Trial 1 and Trial 2 were performed on day 7.

(2-2) Test Results

Figure 4:
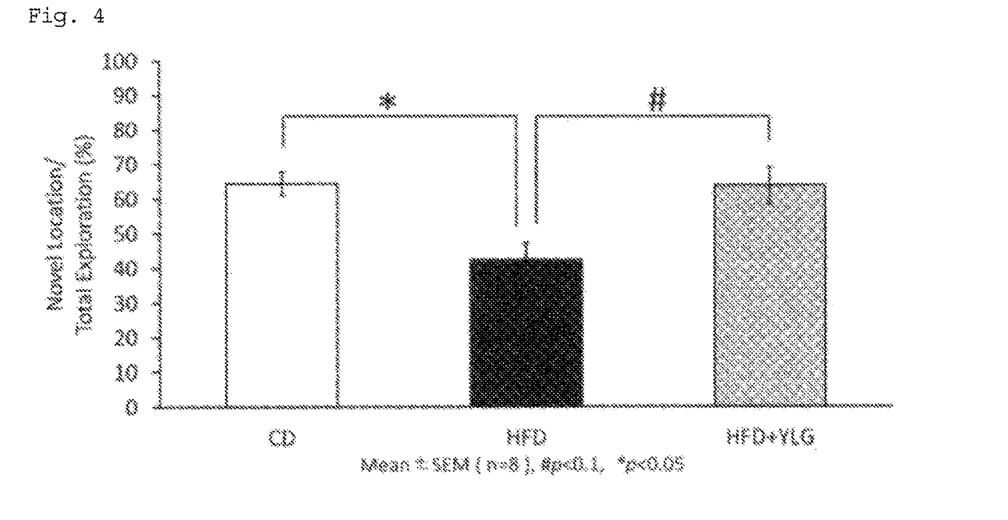
FIG. 4 shows the results of the OLT. The results are expressed as a ratio (%) of the approach time for an object placed in a novel location to the total approach time for two objects placed in a square open field (vertical axis).

FIG. 4 shows the test results. As shown in FIG. 4, the results of the object location test (OLT), which evaluates spatial memory, clarified that the high-fat diet group (HFD group) showed a decrease in the approach time for the object placed at the novel location (cognitive function deteriorated), compared to the normal diet group (CD group). However, the group administered a high-fat diet and the YLG (HFD+YLG group), in which the YLG peptide was orally administered daily while the high-fat diet was fed, showed an increase in the approach time, and its level recovered to a level equal to that of the normal diet group (CD group) (cognitive function improved). This suggests that oral administration of the YLG peptide improves spatial memory decreased by a high-fat diet.

(3) Hippocampal Neurogenesis Evaluation Test Using Deoxyuridine Bromide (3-1) Test Method On day 6 after the initiation of feeding, 100 mg/kg of deoxyuridine bromide (BrdU) was intraperitoneally administered to the mice of each group (n=4), and after 24 hours (day 7), perfusion fixation was performed using 4% paraformaldehyde. Next, the whole brain was extracted and frozen to prepare frozen sections on a cryostat. The prepared frozen sections were immunofluorescently stained with an anti-BrdU antibody (Abcam), and then the number of BrdU-positive cells in the hippocampal dentate gyrus was counted under a fluorescence microscope to evaluate hippocampal neurogenesis. In dementia patients, hippocampal neurogenesis is decreased; however, it is known that administration of a dementia therapeutic agent, such as acetylcholinesterase inhibitors, increases hippocampal neurogenesis.

(3-2) Test Results

Figure 5:
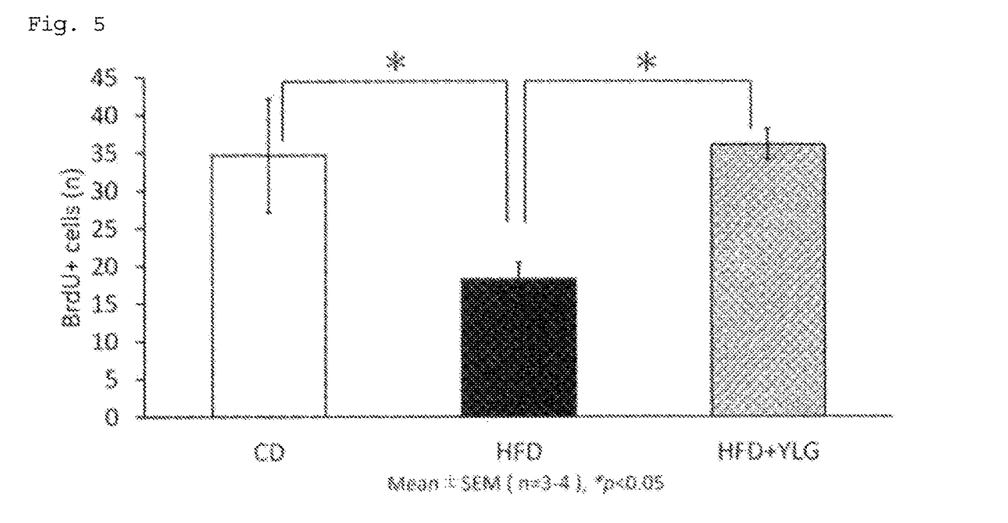
FIG. 5 is a graph showing the results of the hippocampal neurogenesis evaluation test conducted in Experimental Example 1 (3) using deoxyuridine bromide. The results are expressed as a number of BrdU-positive cells in the dentate gyrus of the hippocampus.

FIG. 5 shows the test results. As shown in FIG. 5, the high-fat diet group (HFD group) showed a decrease in the number of BrdU positive cells, and a decrease in hippocampal neurogenesis was observed (cognitive function deteriorated), compared to the normal diet group (CD group). However, the group administered a high-fat diet and the YLG (HFD+YLG group), in which the YLG peptide was orally administered daily while the high-fat diet was fed, showed an increase in the number of BrdU positive cells, and its level recovered to a level equal to that of the normal diet group (the CD group) (cognitive function improved). This suggests that oral administration of the YLG peptide promotes and increases hippocampal neurogenesis decreased by a high-fat diet, and improves cognitive function.

(4) Brain-Derived Neurotrophic Factor (BDNF) mRNA Expression Measurement Test (4-1) Test Method On day 7 after the initiation of feeding, the mice in each group (n=8) were dissected under anesthesia, and the hippocampus was removed from the brain. The removed hippocampus was stored in RNA later for RNA extraction. RNA was extracted from the hippocampus according to a standard method, and cDNA was synthesized. Then, the brain-derived neurotrophic factor (BDNF) mRNA expression level in the hippocampus was measured by RT-PCR according to a standard method. The BDNF mRNA expression level in the hippocampus was standardized with the β-actin mRNA expression level in the hippocampus in a similar manner.

(4-2) Test Results

Figure 6:
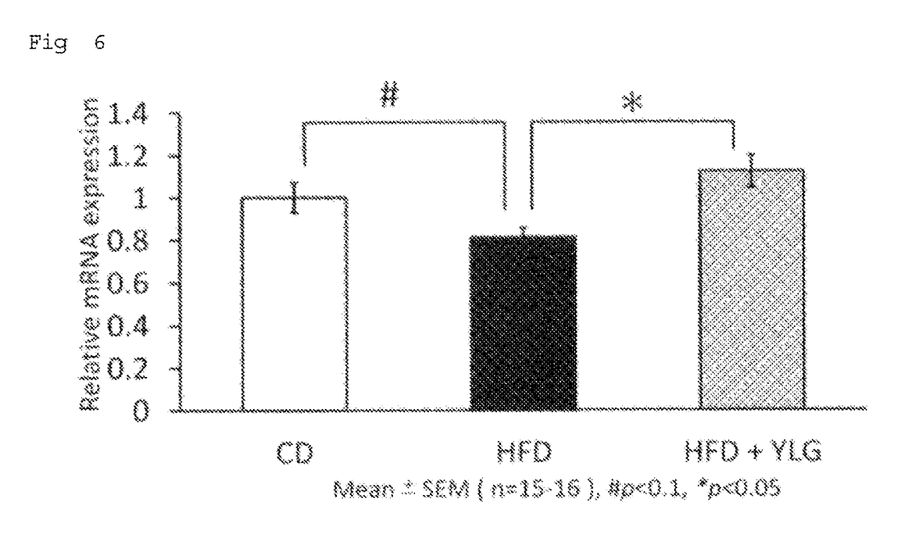
FIG. 6 is a graph showing the results of a measurement test of brain-derived neurotrophic factor (BDNF) mRNA expression level conducted in Experimental Example 1 (4). The results are expressed as a BDNF mRNA expression level in the hippocampus.

FIG. 6 shows the test results. As shown in FIG. 6, the results clarified that the high-fat diet group (HFD group) showed a decrease in the BDNF mRNA expression level in the hippocampus, compared to the normal diet group (CD group). However, the group administered a high-fat diet and the YLG (HFD+YLG group), in which the YLG peptide was orally administered daily while the high-fat diet was fed, showed an increase in the BDNF mRNA expression level, and its level recovered to a level equal to or even greater than that of the normal diet group (CD group). The results clarified that administration of the YLG peptide increases BDNF expression involved in neurogenesis.

The results of the tests using model animals with deteriorated cognitive function obtained by feeding a short-term high-fat diet to decrease hippocampus-dependent memory confirmed that oral administration of the YLG peptide, which is a tripeptide from αs-casein (a major protein in milk), improves hippocampus-dependent memory decreased by a high-fat diet. Promotion of hippocampal neurogenesis and an increase in BDNF expression are believed to particularly contribute to this improvement.

Experimental Example 2: Glucose and Insulin Tolerance Test (1) Test Method (1-1) Glucose Tolerance Test Twelve-week-old male dd Y mice were divided into 3 groups (n=8). The mice were reared for 1 week such that Group 1 was fed a normal diet (3.85 kcal/g: 20 kcal % of protein, 70 kcal % of carbohydrate, and 10 kcal % of lipid), and Group 2 and Group 3 were fed a 60% high-fat diet (5.24 kcal/g: 20 kcal % of protein, 20 kcal % of carbohydrate, and 60 kcal % of lipid). During the period, the YLG peptide was orally administered to Group 3 daily in an amount of 10 mg/kg/day.

Group 1: normal diet group (CD group)
Group 2: high-fat diet group (HFD group)
Group 3: high-fat diet+YLG administration group (HFD+YLG group)

On day 7 after the initiation of feeding, glucose (2 g/kg/p.o.) was administered after fasting for 5 hours. The administration of the YLG peptide on day 7 was performed 2 hours before the glucose administration. Blood was collected from the tail vein immediately before the glucose administration, and 15 minutes, 30 minutes, and 60 minutes after the administration to measure the blood glucose level using a glucose sensor (Nipro Corporation).

(1-2) Insulin Tolerance Test

As in the glucose tolerance test, twelve-week-old male dd Y mice were divided into 3 groups (n=6-7), and the mice were reared for 1 week such that Group 1 was fed a normal diet, and Group 2 and Group 3 were fed a 60% high-fat diet. During the period, the YLG peptide was orally administered to Group 3 daily in an amount of 10 mg/kg/day. On day 7 after the initiation of feeding, insulin (0.5 U/kg/i.p.) was administered after fasting for 5 hours. The administration of the YLG peptide on day 7 was performed 2 hours before the insulin administration. Blood was collected from the tail vein immediately before insulin administration, and 15 minutes, 30 minutes, and 60 minutes after the administration to measure the blood glucose level using a glucose sensor (Nipro Corporation).

(2) Test Results

Tables 1 and 2 show changes in blood glucose level in the glucose tolerance test and changes in blood glucose level in the insulin tolerance test, respectively. The numerical values shown in each table are relative values, taking the blood glucose level immediately before the administration of glucose or insulin as 100.

TABLE 1

|        | CD        | HFD       | HFD + YLG  |
|--------|-----------|-----------|------------|
| 15 min | 172 ± 7*  | 247 ± 23  | 190 ± 14*  |
| 30 min | 135 ± 6*  | 201 ± 22  | 169 ± 10   |
| 60 min | 113 ± 5*  | 143 ± 11  | 113 ± 5*   |

*P < 0.05 vs HFD

As shown in Table 1, the high-fat diet intake resulted in an increase in blood glucose level (HFD group); however, the administration of the YLG peptide prevented the increase in blood glucose level (HFD+YLG group).

TABLE 2

|        | CD      | HFD     | HFD + YLG |
|--------|---------|---------|-----------|
| 15 min | 97 ± 5  | 95 ± 3  | 90 ± 2    |
| 30 min | 84 ± 6  | 88 ± 3  | 78 ± 3    |
| 60 min | 78 ± 5  | 85 ± 3  | 70 ± 4*   |

*P < 0.05 vs HFD

As shown in Table 2, the high-fat diet intake slightly induced insulin resistance (HFD group); however, the administration of the YLG peptide showed an improvement (HFD+YLG group). The overall results of the glucose tolerance test and the insulin tolerance test confirmed that the administration of the YLG peptide improved insulin resistance induced by the high-fat diet.

The results of Experimental Example 2 suggest that the YLG peptide has an effect in terms of improving insulin resistance and improving diabetes, and is thus useful as an active ingredient of anti-diabetic compositions. Therefore, the present invention can provide an anti-diabetic composition comprising an YLG peptide. Further, the present invention can provide use of an YLG peptide in the manufacture of an anti-diabetic composition, an YLG peptide or YLG peptide-containing composition for improving diabetes, a method for improving insulin resistance in a subject suffering from insulin resistance, the method comprising administering an YLG peptide or YLG peptide-containing composition to the subject, or a method for improving diabetes.

Alzheimer's disease is also referred to as brain insulin resistance. It is known that insulin sensitivity and Alzheimer's disease are closely associated with each other (NPL 5). The above results demonstrated that the YLG peptide has an effect in terms of improving insulin resistance; thus, it is possible that the YLG peptide improves deteriorated cognitive function through the action on insulin resistance.

The invention claimed is:

1. A method for improving insulin resistance, preventing deterioration in cognitive function, and improving cognitive function in a subject with insulin resistance and with deterioration in cognitive function, or a subject with insulin resistance and with signs of deterioration in cognitive function, the method comprising administering a tripeptide represented by Tyr-Leu-Gly or a composition comprising the tripeptide to the subject.

2. The method according to claim 1, wherein the composition is a food composition, a food additive composition, or a pharmaceutical composition.

3. The method according to claim 2, wherein the food composition is a health food, a functional food, a dietary supplement, a supplement, a health-promoting food, a food for specified health use or a food for the sick.

4. The method according to claim 1, wherein the insulin resistance is induced by intake of a high-fat diet.

5. The method according to claim 1, wherein the subject with insulin resistance is an Alzheimer's patient.

6. The method according to claim 1, wherein the cognitive function is a brain function relating to episodic memory and/or spatial memory.

7. The method according to claim 1, wherein the improvement in insulin resistance and the improvement in cognitive function are an improvement of insulin sensitivity decreased by intake of a high-fat diet and an improvement of deteriorated cognitive function.

8. The method according to claim 1, wherein the subject with insulin resistance is a diabetic patient and wherein the method is for improving diabetes by preventing deterioration in cognitive function, improving cognitive function, and improving insulin resistance.

* * * * *